US011219720B2

(12) United States Patent
Lewkonya et al.

(10) Patent No.: US 11,219,720 B2
(45) Date of Patent: Jan. 11, 2022

(54) SAFETY NEEDLE WITH NEEDLE HUB, AND METHODS OF USE THEREOF

(71) Applicants: Gad Lewkonya, Neve Mivtach (IL); David Daily, Herzliya (IL); Lior Raday, Kibbutz Bror-Hail (IL)

(72) Inventors: Gad Lewkonya, Neve Mivtach (IL); David Daily, Herzliya (IL); Lior Raday, Kibbutz Bror-Hail (IL)

(73) Assignee: DALI MEDICAL DEVICES LTD., Yavne (IL)

( * ) Notice: Subject to any disclaimer, the term of this patent is extended or adjusted under 35 U.S.C. 154(b) by 143 days.

(21) Appl. No.: 16/594,032

(22) Filed: Oct. 6, 2019

(65) Prior Publication Data

US 2020/0108210 A1 Apr. 9, 2020

Related U.S. Application Data

(60) Provisional application No. 62/742,460, filed on Oct. 8, 2018.

(51) Int. Cl.
*A61M 5/32* (2006.01)

(52) U.S. Cl.
CPC ........ *A61M 5/3245* (2013.01); *A61M 5/3293* (2013.01)

(58) Field of Classification Search
CPC .............. A61M 5/3245; A61M 5/3293; A61M 5/3272; A61M 5/3202; A61M 2005/3267; A61M 5/326; A61M 5/20; A61M 5/3271
See application file for complete search history.

(56) References Cited

U.S. PATENT DOCUMENTS

| | | | |
|---|---|---|---|
| 2002/0004648 A1* | 1/2002 | Larsen | A61M 5/326 604/195 |
| 2003/0014019 A1* | 1/2003 | Saied | A61M 5/282 604/240 |
| 2006/0189933 A1* | 8/2006 | Alheidt | A61M 5/326 604/110 |
| 2012/0041368 A1* | 2/2012 | Karlsson | A61M 5/3272 604/111 |
| 2014/0025015 A1* | 1/2014 | Cross | A61M 5/3294 604/198 |
| 2015/0182691 A1* | 7/2015 | McLoughlin | A61M 5/002 604/155 |

FOREIGN PATENT DOCUMENTS

WO WO-2017077537 A1 * 5/2017 ............ A61M 5/326

* cited by examiner

*Primary Examiner* — William R Carpenter
(74) *Attorney, Agent, or Firm* — Naomi S. Rosenman-Helfand

(57) ABSTRACT

A needle protection system, adapted to protect a tip of a hypodermic needle connected or connectable to a syringe. The system comprises a shield to shield the tip of the needle; a needle hub engaged to the hypodermic needle and having an exterior surface including at least one slot. The slot includes at least three surfaces corresponding to three operative orientations of said shield. The needle hub is connected to the shield such that the shield can move axially, but cannot rotate, relative to the needle hub. The three operative orientations include a storage operative orientation, an injection operative orientation, and a needle protection operative orientation. The system also includes a locking sleeve, at least one biasing element, a needle sheath, and at least one tab in the slot to prevent undesired movement between said surfaces.

15 Claims, 9 Drawing Sheets

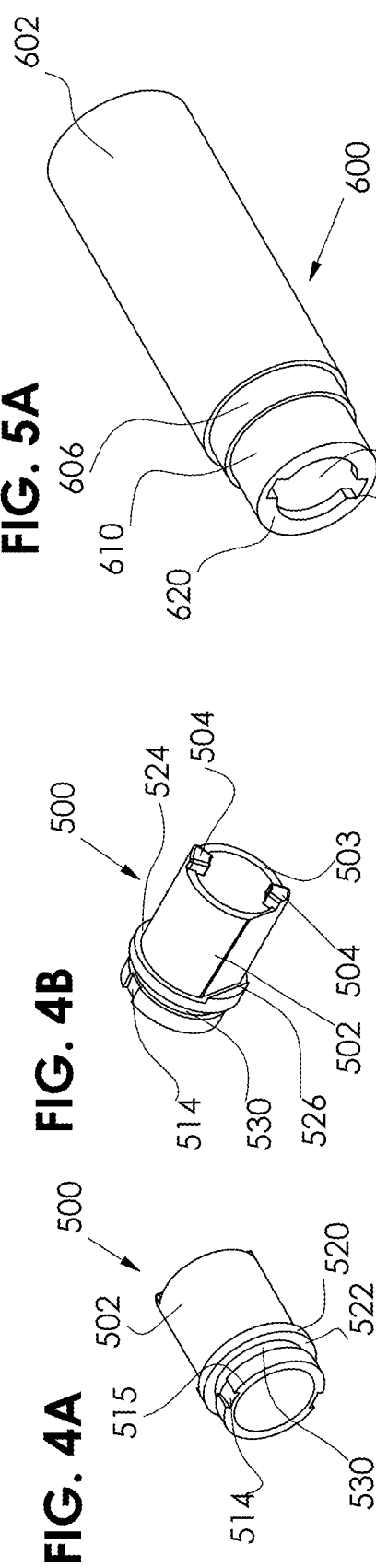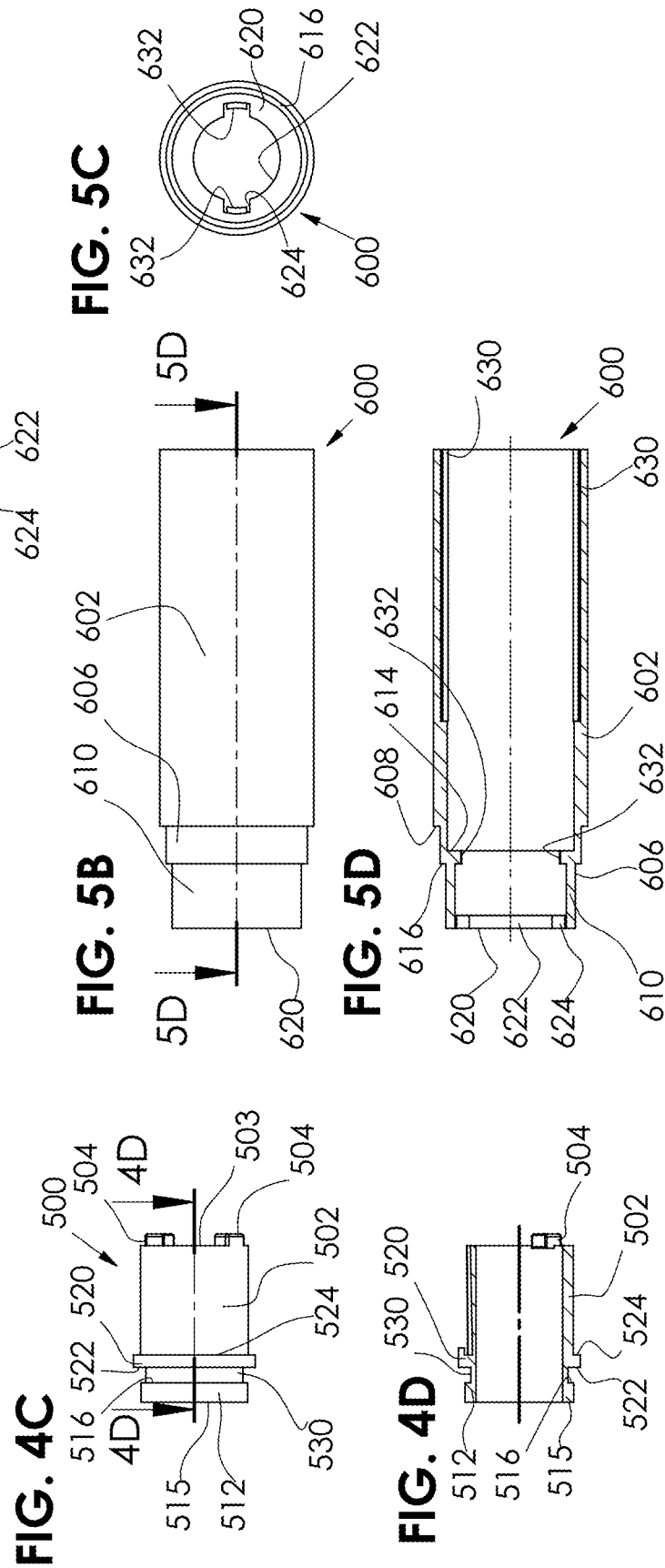

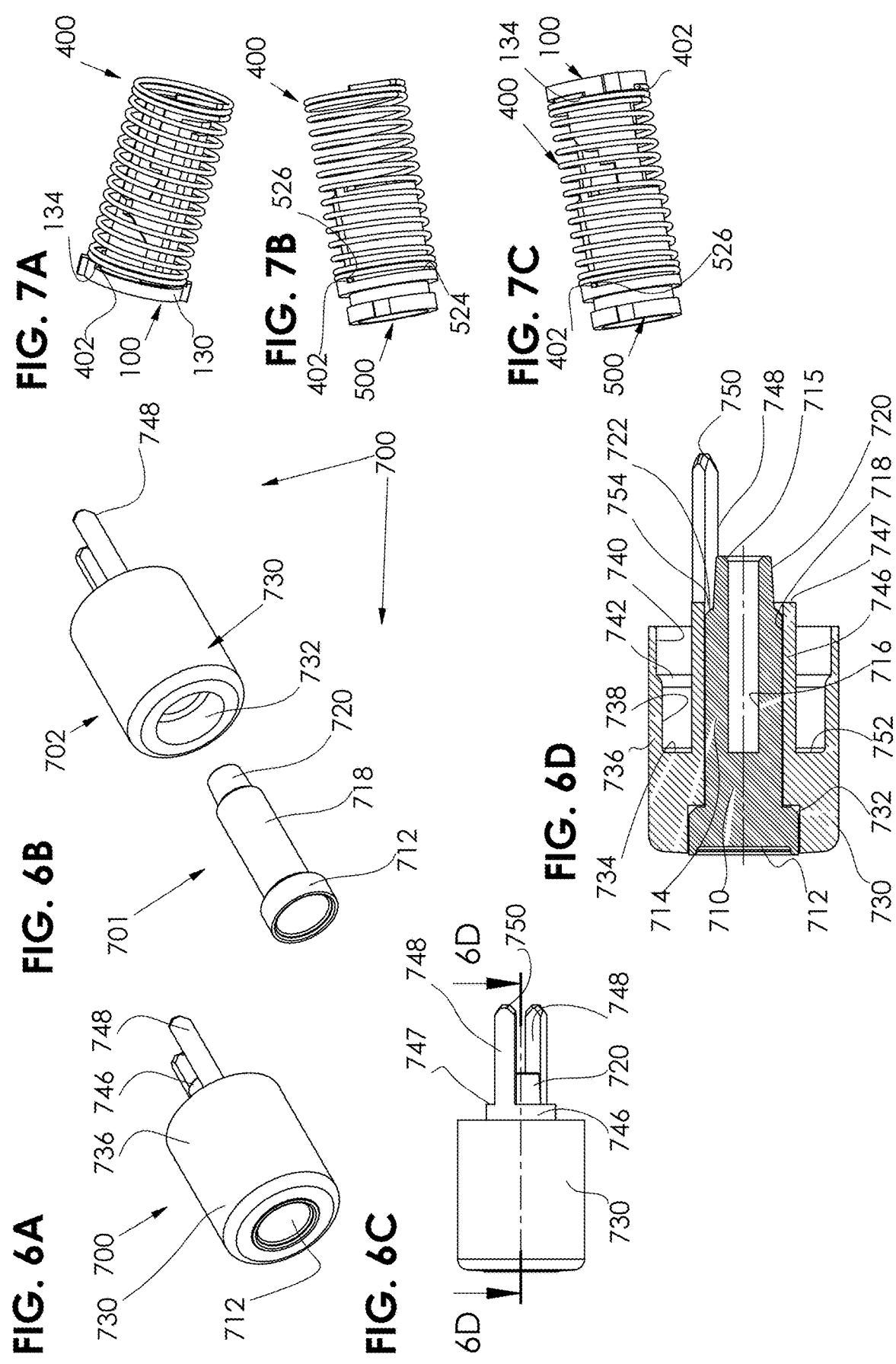

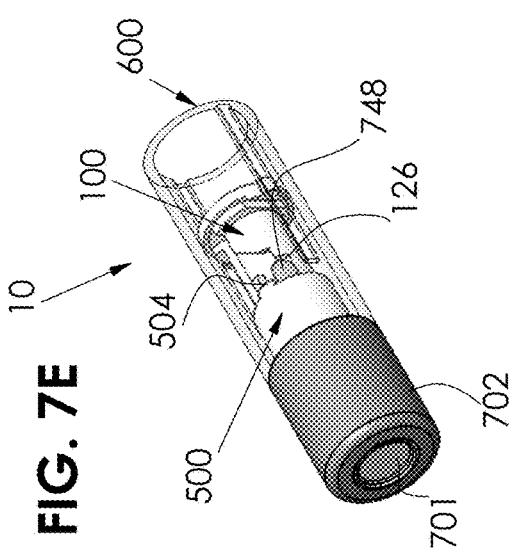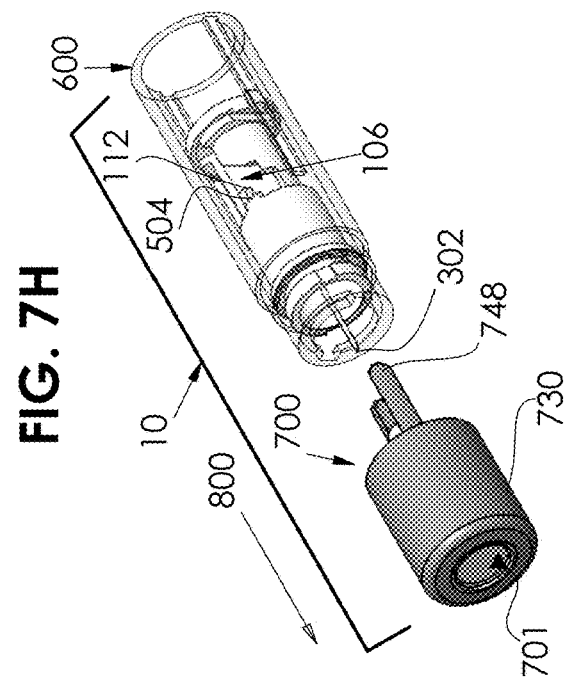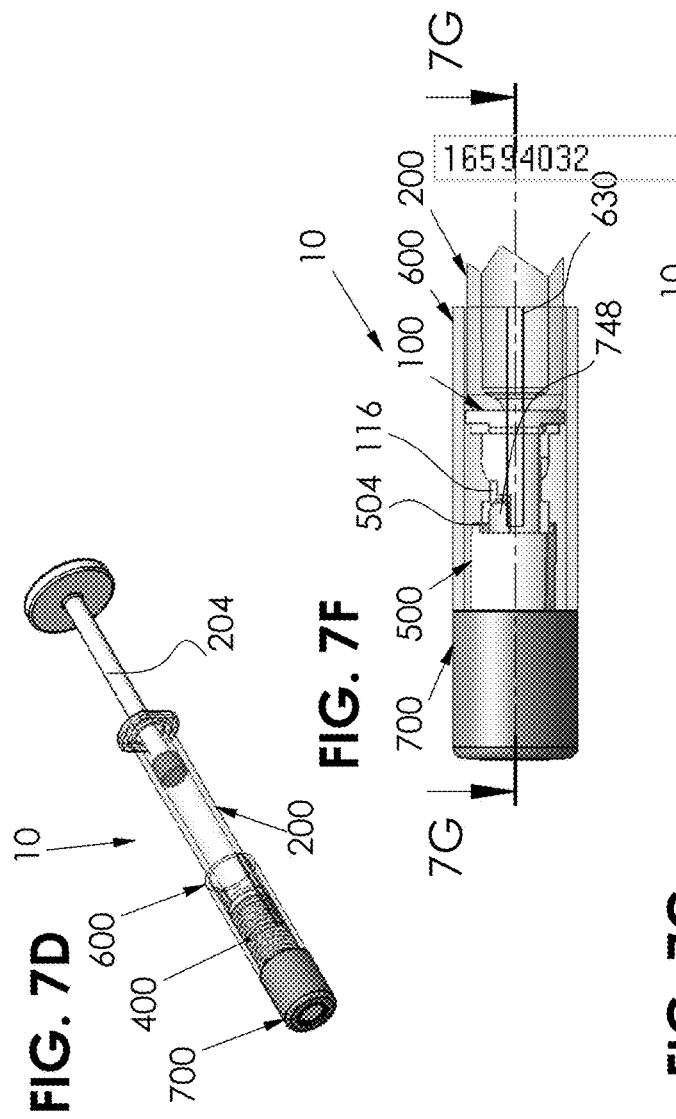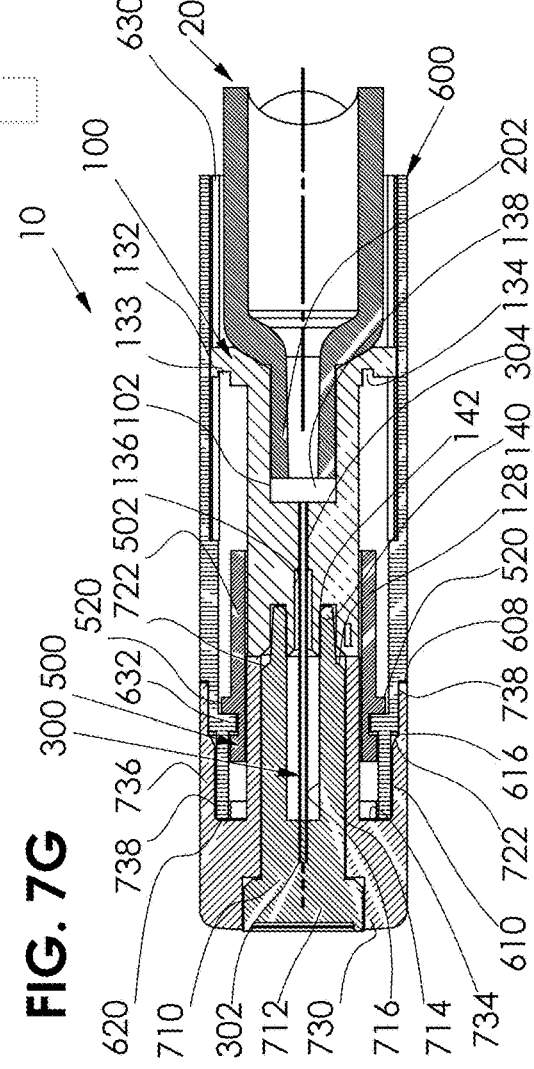

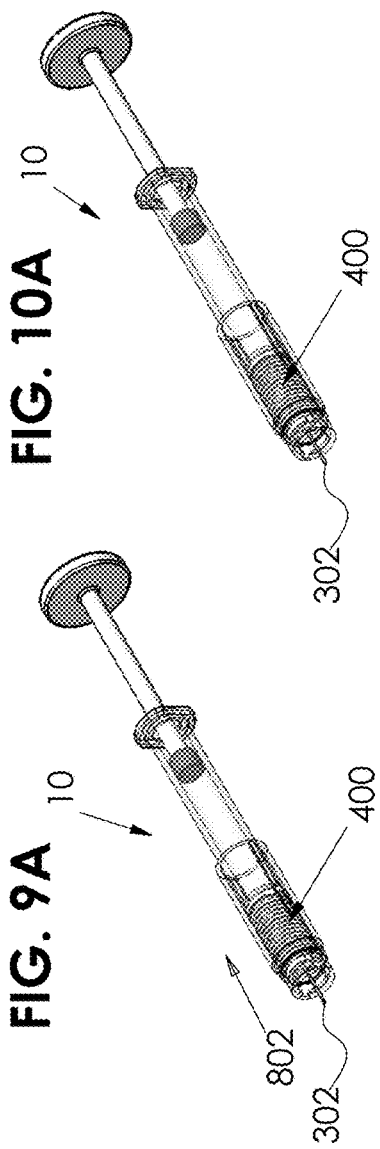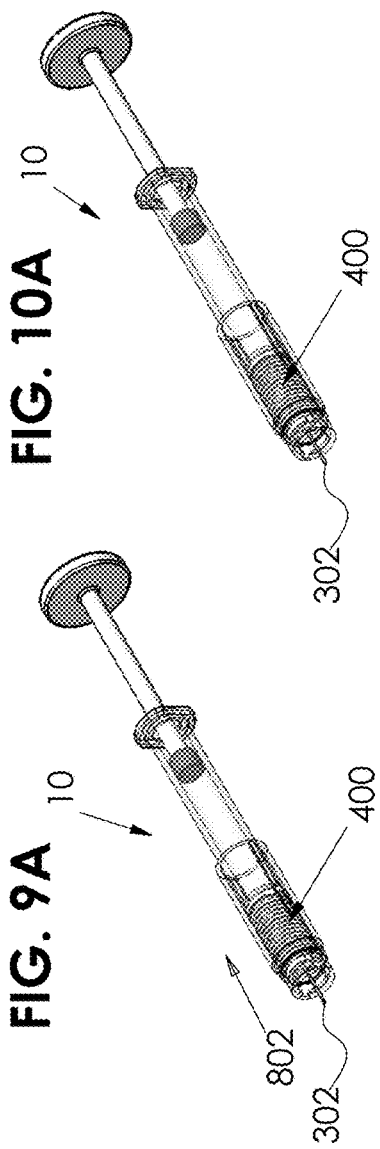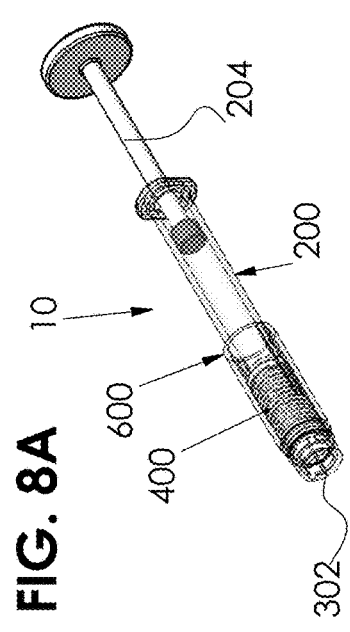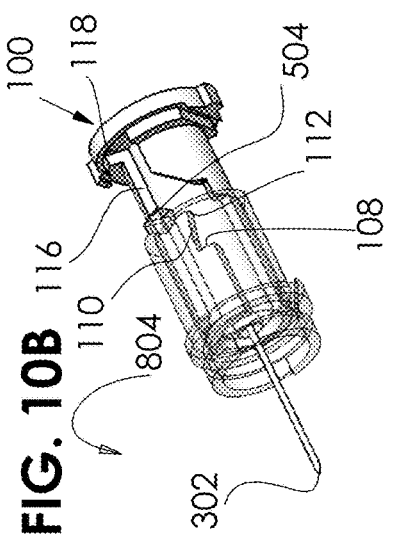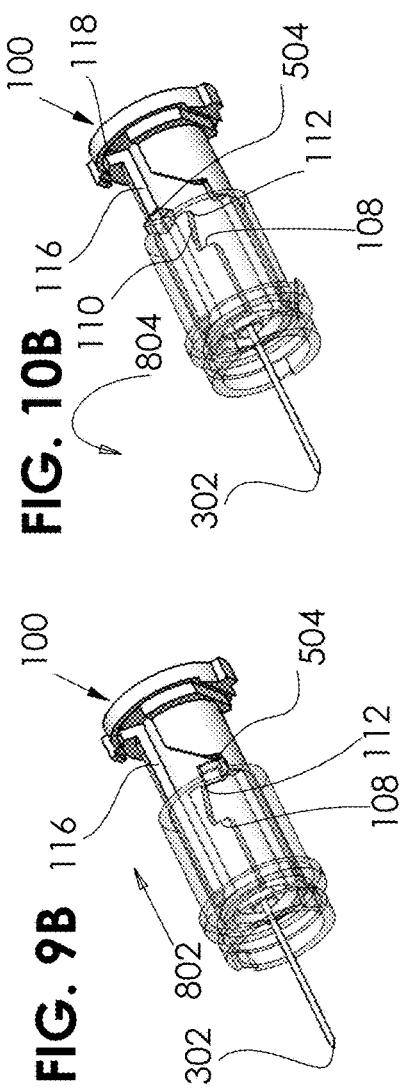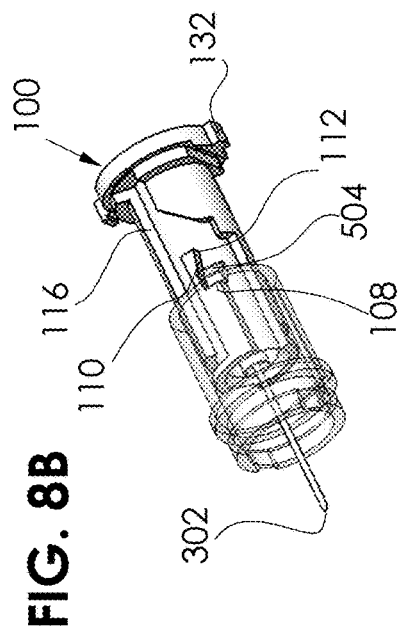

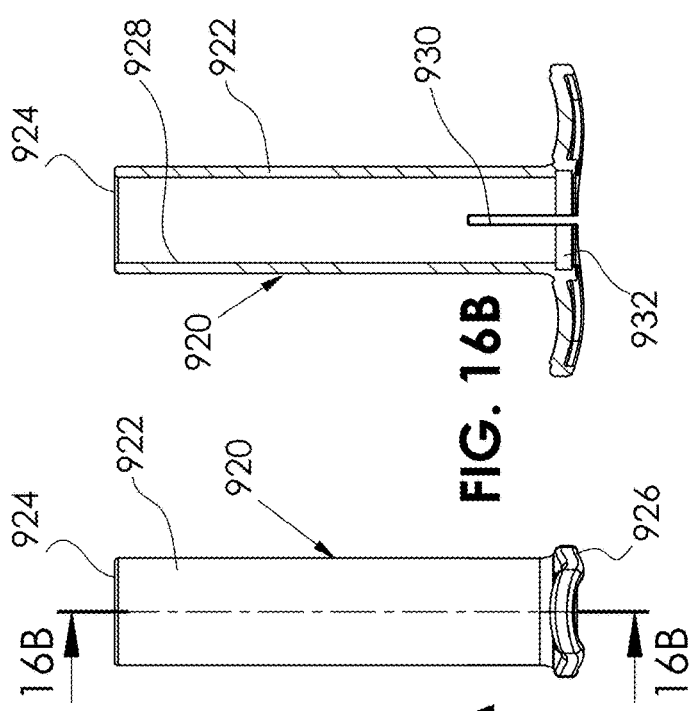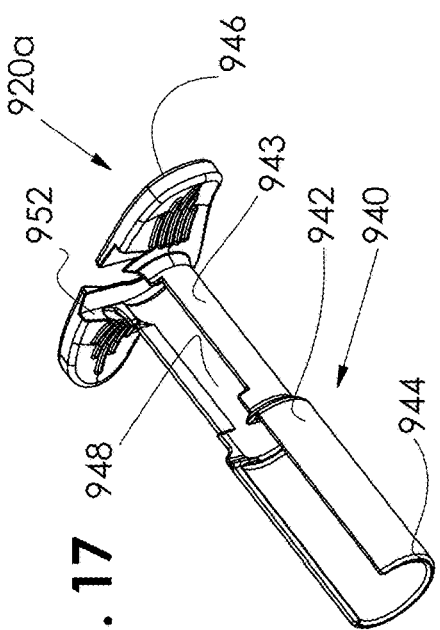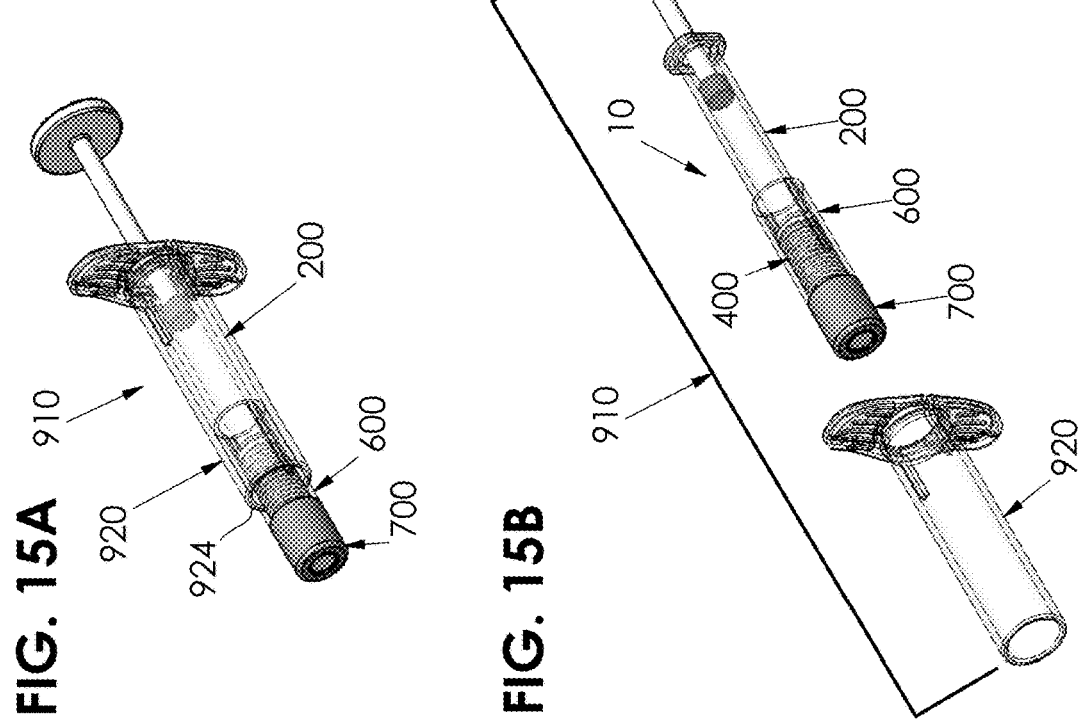

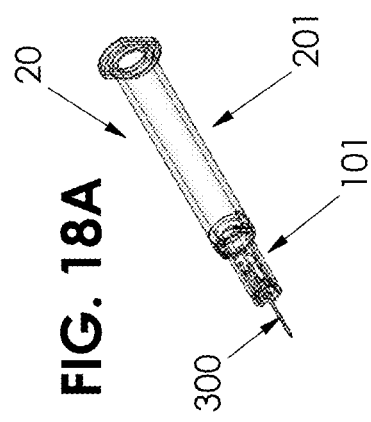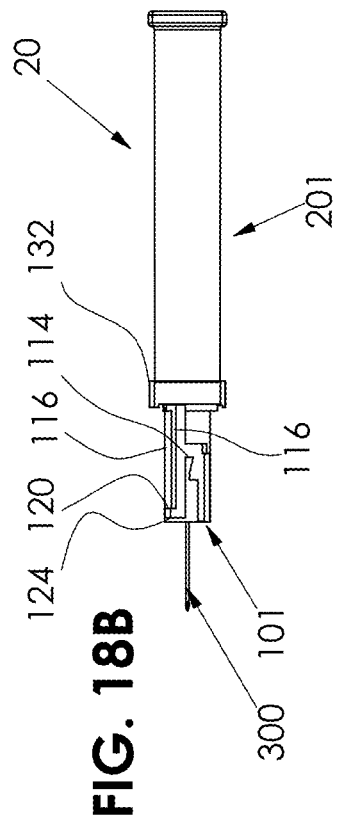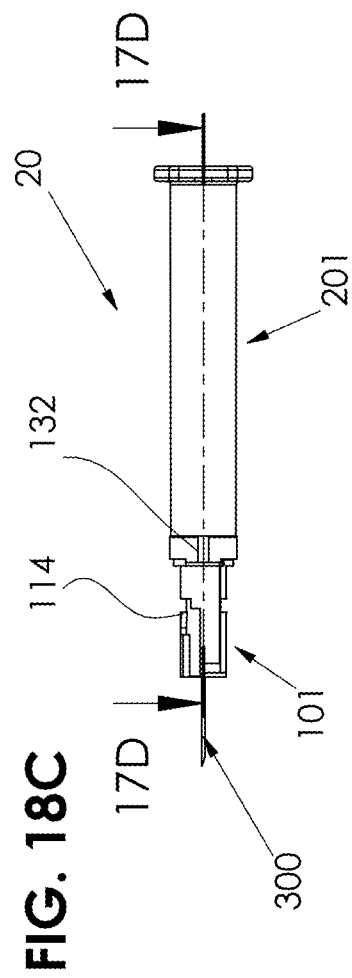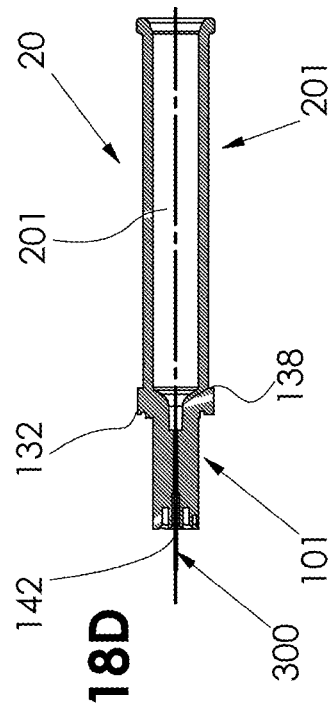

SAFETY NEEDLE WITH NEEDLE HUB, AND METHODS OF USE THEREOF

FIELD AND BACKGROUND OF THE INVENTION

The invention, in some embodiments, relates to the field of injection devices, and more specifically to safety needles and/or to protection of needles that may be pre-connected, by the manufacturer, or connectable, by the end-user, to a syringe.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIGS. 4A and 4B are perspective view illustrations of a locking sleeve forming part of the system of FIG. 1;

FIG. 4C is a side view planar illustration of the locking sleeve of FIGS. 4A and 4B;

FIG. 4D is a sectional illustration of the locking sleeve of FIGS. 4A to 4C, the sectional illustrations taken along respective section lines 4D-4D in FIG. 4C;

FIG. 5A is a perspective view illustration of a shield forming part of the system of FIG. 1;

FIGS. 5B and 5C are, respectively, a side view planar illustration and a front view planar illustration of the shield of FIG. 5A;

FIG. 5D is a sectional illustration of the shield of FIGS. 5A to 5C, the sectional illustrations taken along respective section lines 5D-5D in FIG. 5B;

FIG. 6A is a perspective view illustration of a needle sheath forming part of the system of FIG. 1;

FIG. 6B is a perspective view exploded illustration of the needle sheath of FIG. 6A FIG. 6C is a side view planar illustration of the needle sheath of FIG. 6A;

FIG. 6D is a sectional illustration of the needle sheath of FIGS. 6A and 6C, the sectional illustrations taken along respective section lines 6D-6D in FIG. 6C;

FIG. 7A is a perspective view illustration of the spring of FIG. 3, constructed on the needle hub of FIGS. 2A to 2E;

FIG. 7B is a perspective view illustration of the spring of FIG. 3, constructed on the locking sleeve of FIGS. 4A to 4D;

FIG. 7C is a perspective view illustration of a construction including the spring of FIG. 3, the needle hub of FIGS. 2A to 2E, and the locking sleeve of FIGS. 4A to 4D;

FIG. 7D is a model perspective view illustration of the system of FIG. 1, in a storage operative orientation;

FIG. 7E is a partial model perspective view illustration the system of FIG. 7D, having the spring and the syringe removed therefrom;

FIG. 7F is a model side view planar illustration of the system illustrated in FIG. 7E;

FIG. 7G is a sectional illustration of the system of FIGS. 7E and 7F, taken along section lines 7G-7G in FIG. 7F;

FIG. 7H is a model perspective view illustration of the system illustrated in FIGS. 7E to 7G, having the needle sheath removed therefrom;

FIG. 8A is a model perspective view illustration of the system of FIG. 1, in a ready for use operative orientation;

FIG. 8B is a model perspective view illustration of the needle hub, the needle, and the locking sleeve of the system of FIG. 8A, in the ready-for-use operative orientation;

FIG. 9A is a model perspective view illustration of the system of FIG. 1, in a triggering operative orientation;

FIG. 9B is a model perspective view illustration of the needle hub, the needle, and the locking sleeve of the system of FIG. 9A, in the triggering operative orientation;

FIG. 10A is a model perspective view illustration of the system of FIG. 1, in a triggering rotation operative orientation;

FIG. 10B is a model perspective view illustration of the needle hub, the needle, and the locking sleeve of the system of FIG. 10A, in the triggering rotation operative orientation;

FIGS. 15A and 15B are, respectively, a partially exploded view illustration and a constructed view illustration of another system for protection of a needle connected or connectable to a syringe according to an embodiment of the teachings herein, including the system of FIGS. 1 to 14 and a gripper;

FIGS. 16A and 16B are, respectively, is a side view planar illustration and a sectional illustration of a first embodiment of the gripper forming part of the system of FIG. 15, the sectional illustration being taken along section lines 16B-16B in FIG. 16A;

FIG. 17 is a perspective view illustration of a second embodiment of the gripper forming part of the system of FIG. 15; and FIGS. 18A to 18D are, respectively, a perspective view illustration, two planar view illustrations, and a sectional illustration of a unified syringe and needle hub usable in a

DESCRIPTION OF SOME EMBODIMENTS OF THE INVENTION

Figure 1:
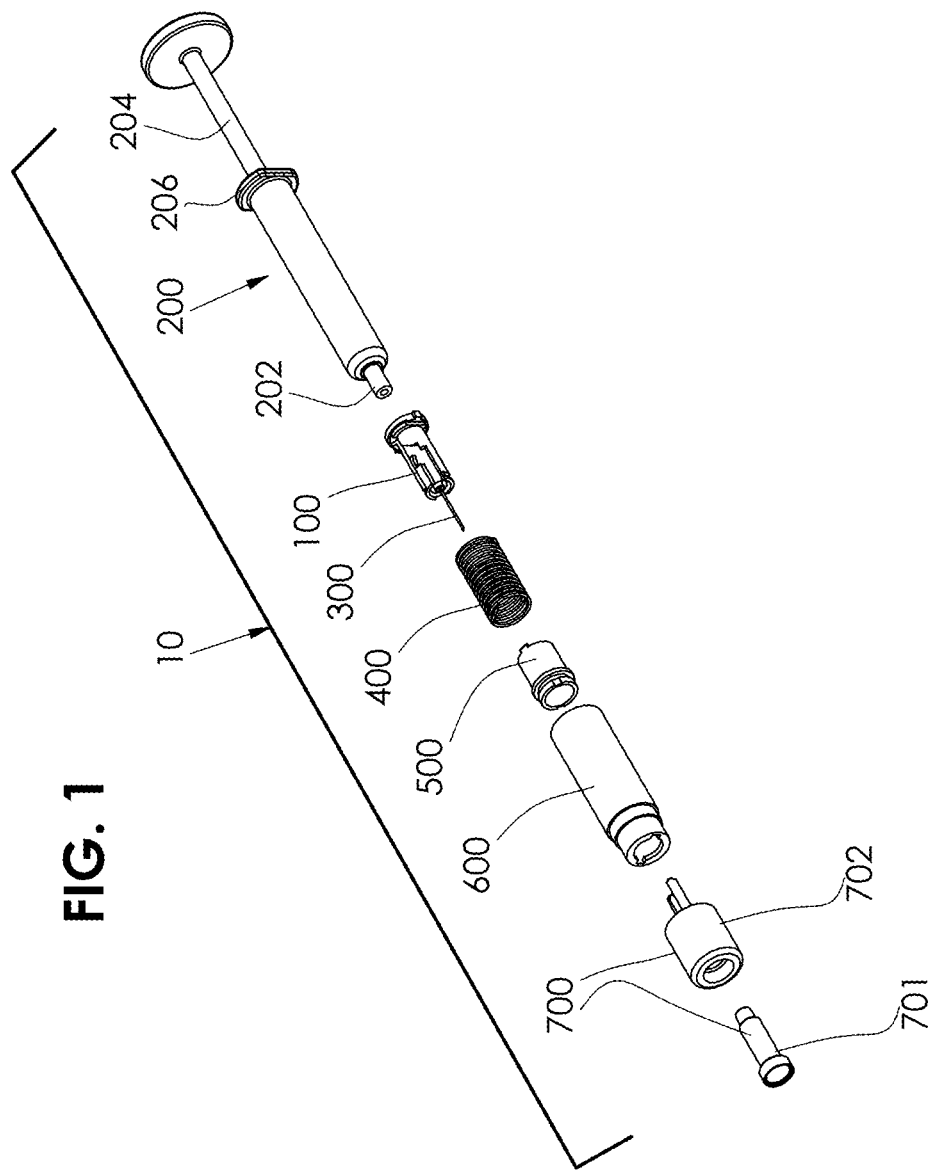
FIG. 1 is an exploded view illustration of a system for protection of a needle connectable to a syringe according to an embodiment of the teachings herein.

The invention, in some embodiments, relates to the field of injection devices, and more specifically to protection of a needle connected or connectable to a syringe. The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings. The invention can be implemented with other embodiments and can be practiced or carried out in various ways. It is also understood that the phraseology and terminology employed herein is for descriptive purpose and should not be regarded as limiting.

In the context of the present application, the terms "forward", "forwardly", and "front" relate to the direction of the needle tip, or to elements that are closer to the needle tip, and the terms "rearward" and "rearwardly" relate to the direction away from the needle tip, or to elements that are farther from the needle tip.

Reference is now made to FIG. 1, which is an exploded view illustration of a system 100 for protection of a needle connected or connectable to a syringe, according to an embodiment of the teachings herein.

As seen in FIG. 1, system 10 includes a needle hub 100, connected or connectable to a tip 202 of a syringe 200. The syringe further includes a plunger 204, as known in the art, terminates rearwardly in a flange 206, and is typically pre-filled. Hub 100 forms a sealed seat for a hypodermic needle 300, which, when syringe 200 is connected to needle hub 100, is in fluid communication with syringe 200. The seal surrounding needle 300 may be formed in any suitable manner, including an O-ring, an elastomer in which the needle is disposed, and the like. Alternatively, the needle may be glued to the hub 100, welded to the hub by ultrasonic welding or any other type of welding, insert-molded with the hub, or connected by any other suitable type of connection. Needle 300 may be any needle known in the art, and terminates in a sharp needle tip 302.

System 100 further includes a compression spring 400, which in some embodiments is also a torsion spring, a locking sleeve 500, a shield 600, and a needle sheath 700, which, in some embodiments, includes an interior portion 701 and an exterior portion 702.

While spring 400 is illustrated and described herein as a compression spring, the system may be designed to use any other suitable biasing element, such as a tension spring, a constant-force spring, an integrally formed plastic spring, or any other resilient element such as a rubber, plastic or elastomeric element.

Figure 2C:
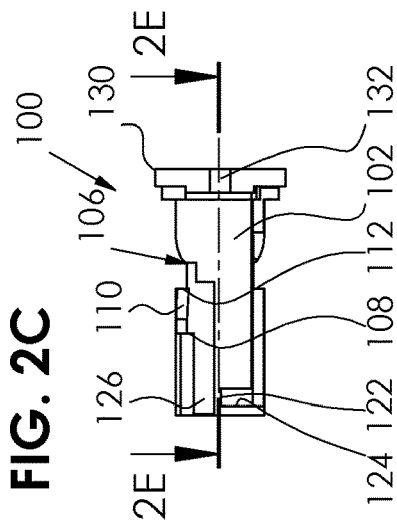
FIGS. 2C and 2D are, respectively, a top view planar illustration and a side view planar illustration of the needle hub of FIGS. 2A and 2B.
Figure 2D:
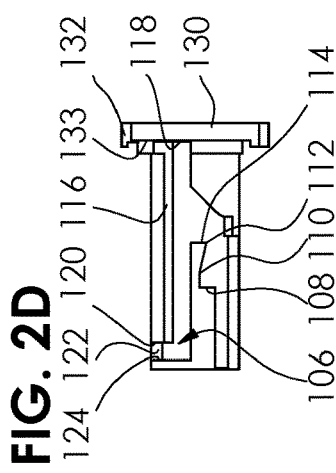
Figure 2E:
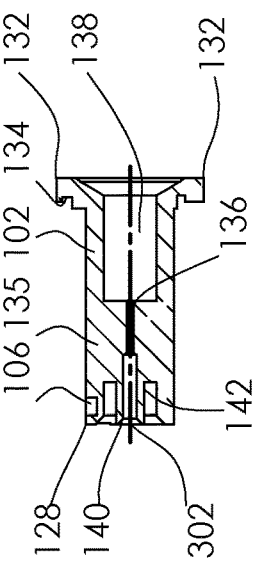
FIG. 2E is a sectional illustration of the needle hub of FIGS. 2A to 2D, the sectional illustrations taken along respective section lines 2E-2E in FIG. 2C.
Figure 2A:
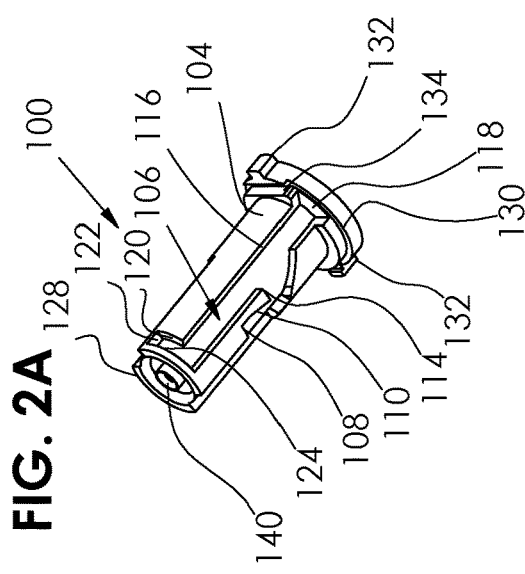
FIGS. 2A and 2B are perspective view illustrations of a needle hub forming part of the system of FIG. 1.
Figure 2B:
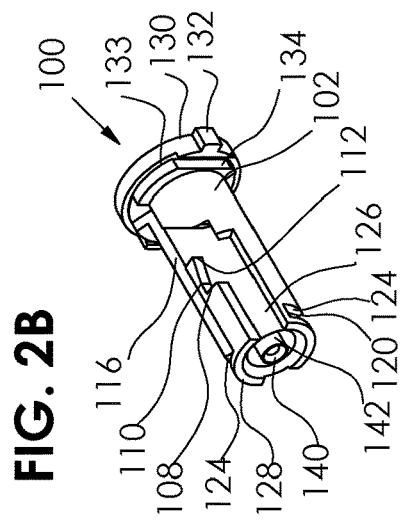

Reference is now made to FIGS. 2A and 2B, are perspective view illustrations of needle hub 100 forming part of system 10, to FIGS. 2C and 2D, which are, respectively, a top view planar illustration and a side view planar illustration of needle hub 100, and to FIG. 2E, which is a sectional illustration of the needle hub 100.

As seen, needle hub 100 includes a longitudinally extending body 102, having an exterior surface 104. Exterior surface 104 has formed thereon one or more guiding slots 106, one of which is seen clearly in FIGS. 2B and 2D. It will be appreciated that though needle hub 100 is illustrated as having a generally cylindrical shape, the needle hub may have a rectangular or any other suitable cross-section, with proper adjustments to other mating parts of system 10.

As explained in further detail hereinbelow, each slot 106 includes multiple surfaces, which define the stages of operation of system 10, and the protection depth. Specifically, slot 106 defines a storage portion including a forward storage surface 108 and a side storage surface 110 terminating at a triggering point 112, a triggering portion including a triggering surface 114, a main slot portion including a torque limiting surface 116 and a range limiting surface 118, and a locking portion including a locking surface 120, an end of rotation surface 122, and a protection surface 124. Each slot 106 further includes, forwardly of the storage portion of the slot, a needle sheath receiving slot 126.

At a forward end thereof, body 102 is generally tubular, and terminates in an end surface 128. At a rearward end thereof, body 102 is generally tubular, and terminates in a base 130, which has a diameter greater than that of body 102. Base 130 includes one or more radially outwardly extending protrusions 132, and a forwardly facing surface 133 including a slot 134. Surface 133 is adapted to form a spring seat, such that an end of spring 400 is received in slot 134, as described in further detail hereinbelow. A central portion 135 of body 102 is generally cylindrical, and has a bore 136 extending therethrough.

Hypodermic needle 300 is adapted to fixed within, and to extend through, bore 136 of needle hub 100, such that a rear end there of is disposed within a bore 138 of the rearward end of body 102. The bore 138 is sized and configured to receive and engage tip 202 of syringe 200, such that needle hub 100 and the syringe 200 are sealed to one another, and is in fluid communication with the syringe barrel. Such sealing can be accomplished by any type of welding, such as ultrasonic welding, by gluing, by using an O-ring or any other type of elastomeric or resilient material, or by any other method of sealing. A cylindrical cowl 140 extends longitudinally forwardly from central portion 135 about bore 136 within body 102, defining a passage for needle 300. A cylindrical seat 142 is defined by an exterior surface of cowl 140, a forward facing surface of central portion 135, and an interior surface of body 102.

Figure 3:
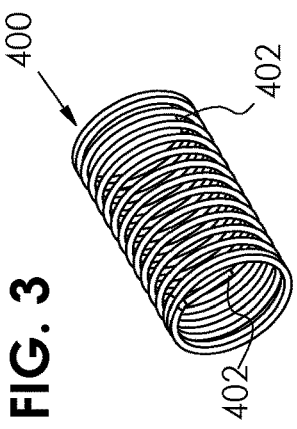
FIG. 3 is a perspective view illustration of a spring forming part of the system of FIG. 1.

Reference is now made to FIG. 3, which is a perspective view illustration of spring 400 forming part of system 10. As seen, spring 400 is a compression spring terminating at either end thereof in a linear portion 402. Linear portion 402 is adapted to engage other components of system 10, to facilitate formation of torque between components of system 10 using spring 400.

Reference is now made to FIGS. 4A and 4B, which are perspective view illustrations of locking sleeve 500 forming part of system 10, to FIG. 4C, which is a side view planar illustration of locking sleeve 500, and to FIG. 4D, which is a sectional illustration of locking sleeve 500.

As seen, locking sleeve 500 includes a hollow, generally cylindrical barrel 502 having a planar portion adapted for passage therealong of linear portion 402 of spring 400, during compression and expansion of the spring as explained hereinbelow. Barrel 502 terminates at a rearward end thereof in a surface 503, having one or more radially inwardly extending guiding teeth 504 extending rearwardly therefrom.

At a forward end thereof, hollow barrel 502 includes a first radially outwardly extending flange 512 having formed therein one or more slots 514 required for assembly of system 10 and defining a forward facing surface 515 and a rearward facing surface 516. Disposed rearwardly of flange 512 is a second, radially outwardly extending circumferential flange 520, including a forward facing surface 522 and a rearward facing surface 524. Surface 524 forms a spring seat, and includes a rearwardly facing slot 526 adapted to receive a linear end 402 of spring 400, as described in further detail hereinbelow. A groove 530 is defined between rearward facing surface 516 of flange 512 and forward facing surface 522 of flange 520, and is adapted to engage a portion of shield 600, as described in further detail hereinbelow.

Reference is now made to FIG. 5A, which is a perspective view illustration of shield 600 forming part of system 10, to FIGS. 5B and 5C which are, respectively, a side view planar illustration and a front view planar illustration of shield 600, and to FIG. 5D, which is a sectional illustration of shield 600.

As seen, shield 600 includes a generally cylindrical body portion 602 terminating, at a rearward end thereof in a surface 604. Extending forwardly from body portion 602 is a generally cylindrical neck portion 606, having the same interior circumference as body portion 602, and a smaller exterior circumference than body portion 602, such that a shoulder 608 is formed between the exterior surfaces of body portion 602 and of neck portion 606.

Extending forwardly from neck portion 606 is a generally cylindrical forward portion 610. Forward portion 610 has smaller interior and exterior circumferences than neck portion 606. A ring-shaped wall portion 612 connects neck portion 606 and forward portion 610, forming a radially inward facing shoulder 614 and a radially outward facing shoulder 616. Forward portion 610 terminates, at a forward end thereof, in a skin engaging surface 620 adapted to engage the skin of the user. Skin engaging surface 620 includes a generally circular bore 622, having one or more slits 624 extending radially outwardly therefrom along a diameter of bore 622.

Extending longitudinally along part of an interior surface of body portion 602, from rearward surface 604 toward shoulder 614, are one or more hub engaging slots 630 adapted to engage protrusions 132 of needle hub 100, as described in further detail hereinbelow. One or more locking sleeve engaging protrusions 632 extend radially inwardly from an interior surface of forward portion 610, adjacent and forwardly of shoulder 614, and are adapted to engage groove 530 of locking sleeve 500 as described in further detail hereinbelow. Protrusions 632 are preferably aligned with slits 624.

Reference is now made to FIG. 6A, which is a perspective view illustration of needle sheath 700 forming part of system 10, to FIG. 6B which is a perspective view exploded illustration of needle sheath 700, to FIG. 6C, which is a side view planar illustration of needle sheath 700, and to FIG. 6D, which is a sectional illustration of the needle sheath 700.

As described hereinabove with reference to FIG. 1, and as shown clearly in FIG. 6B, in some embodiments, needle sheath 700 may include an interior portion 701 and an exterior portion 702. In other embodiments, interior and exterior portions 701 and 702 may be formed as a single unit, or may be molded over one another.

Interior portion 701 includes a generally cylindrical body portion 710, terminating, at a forward end thereof, in a base 712 having a greater circumference than body portion 710. Extending rearwardly from body portion 710 is a tubular sleeve 714, preferably having the same circumference as body portion 710 and terminating at a rearward end thereof in a circular surface 715. Sleeve 714 has an interior surface 716, which in the illustrated embodiment has a fixed diameter, though in other embodiments surface 716 may be tapered. Sleeve 714 further has an exterior surface including a first portion 718 having a first diameter, a second portion 720, disposed rearwardly of first portion 718, having a second, smaller, diameter, and a slanted shoulder 722 connecting first portion 718 and second portion 720. Interior portion 701 is formed of an elastomeric material, and is typically formed as a single unit, for example molded in the desired shape.

Exterior portion 702 includes a generally cylindrical body portion 730, defining a hollow bore 732 adapted to receive body portion 710 and base 712 of interior portion 701. As such, bore 732 includes a first portion having a greater circumference which receives base 712, and a second portion having a smaller circumference which receives body portion 710. At a rearward end thereof, body portion 730 terminates in a wall portion 734. Extending rearwardly from wall portion 734, around a circumference thereof, is a sleeve portion 736 having an exterior surface flush with the exterior surface of body portion 730, and an interior surface including a first portion 738 having a first diameter, a second portion 740, disposed rearwardly of first portion 738, having a second, larger, diameter, and a slanted shoulder 742 connecting first portion 738 and second portion 740.

Extending rearwardly from wall portion 734, within sleeve portion 736 and concentric therewith, is a second sleeve portion 746, sized and configured to receive and engage sleeve portion 714 of first portion 701. Sleeve portion 746 terminates, at a rearward end thereof, in a wall portion 747. One or more tabs 748, here shown as a pair of tabs, extend from a rearward end of sleeve portion 746 on opposing sides thereof, and terminate in a generally trapezoidal end 750.

A first circumferential seat 752 is defined between an interior surface of sleeve portion 736, and an exterior surface of sleeve portion 746, against wall portion 734. A second circumferential seat 754 is defined between an interior surface of sleeve portion 746 and tabs 748, second portion 720 of the exterior surface of tubular sleeve 714, against slanted shoulder 722 of tubular sleeve 714.

The construction of system 100 in a storage operative orientation will now be explained making additional reference to FIG. 7A to 7H.

FIGS. 7A to 7C illustrate the arrangement of spring 400 within the system 10. Specifically, FIG. 7A is a perspective view illustration of spring 400 constructed onto needle hub 100, FIG. 7B is a perspective view illustration of spring 400 constructed onto locking sleeve 500, and FIG. 7C is a perspective view illustration of a construction including spring 400, needle hub 100, and locking sleeve 500.

As seen in FIGS. 7A and 7C, one end of compression spring 400 is seated on forward facing surface 133 of base 130 of needle hub 100, such that a first linear portion 402 of the spring is held within slot 134 of base 130. Similarly, an opposing end of compression spring 400 is seated on rearward facing surface 524 of flange 520 of locking sleeve 500, such that a second linear portion 402 of the spring is held within slot 526 of flange 520, as seen in FIGS. 7B and 7C. Engagement of linear portions 402 of spring 400 within slots 134 and 526 allows providing a torque load to spring 400, during construction of system 10. Following construction, compression spring 400 is disposed about body 102 of hub 100 and barrel 502 of sleeve 500, and forward pushing force and torsion load of spring 400 are applied to locking sleeve 500.

Turning now to FIGS. 7D to 7H, FIG. 7D is a model perspective view illustration of the system 10 in the storage operative orientation, FIG. 7E is a partial model perspective view illustration of system 10, having spring 400 and syringe 200 removed therefrom, FIG. 7F is a model side view planar illustration of system 10 as shown in FIG. 7D, FIG. 7G is a sectional illustration of system 10 as shown in FIG. 7D, and to FIG. 7H is a model perspective view illustration of system 10 as shown in FIG. 7D, having the needle sheath 700 removed therefrom.

In the constructed arrangement of system 10, syringe 200 is connected to needle hub 100 such that tip 202 thereof is seated within bore 138 at the rear of hub 100. The connection between needle hub 100 and tip 202 of syringe 200 may be formed in any suitable manner, including snap fit engagement, laser welding, ultrasonic welding, adhesive, overmolding, or any other suitable mechanism. An O-ring or any alternative elastomeric seal may be placed between the needle hub 100 and tip 202 of syringe 200 to seal the connection thereof. The hub 100 may also be formed unitarily with syringe 200, as described hereinbelow with respect to FIGS. 18A to 18D. In some embodiments, the syringe is a pre-filled syringe. In such embodiments, the plunger 204 of the syringe is disposed in a rearward portion of the syringe 200, as shown in FIG. 7D.

As seen in FIG. 7G, hypodermic needle 300 is disposed within bore 136 of needle hub 100, such that a rear end 304 of the needle is disposed within, or is in fluid communication, with syringe 200. Needle 300 extends forwardly out of needle hub 100, at the center of cylindrical cowl 140.

Barrel 502 of locking sleeve 500 is disposed partially about a forward portion of needle hub 100, such that inwardly extending guiding teeth 504 of sleeve 500 engage and rest against forward storage surface 108 of guiding slots 106 of body 102 of needle hub 100.

Shield 600 is disposed about needle hub 100 and locking sleeve 500, such that needle tip 302 projects slightly forwardly of skin engaging surface 620 of the shield, via circular bore 622. Protrusions 132 of base 130 of hub 100 are slidably disposed within hub engaging slots 630 of the shield, such that the shield can move longitudinally relative to the needle hub, but cannot rotate relative to the needle hub. Locking sleeve engaging protrusions 632 of shield 600 are disposed within groove 530 of locking sleeve 500, such that interior shoulder 614 of shield 600 engages forward facing surface 522 of flange 520 of locking sleeve 500. As such, locking sleeve 500 can rotate relative to shield 600.

It will be appreciated that the exact location of forward storage surface 108 of slot 106 determines the extent to which locking sleeve 500 and shield 600 extend forwardly relative to hub 100, and thus the extent to which needle tip 302 protrudes from shield 600. Specifically, when forward storage surface 108 is located closer to the forward end of needle hub 100, the needle tip 302 protrudes to a lesser extent from shield 600, and when forward storage surface 108 is located closer to the rearward end of hub 100, the needle tip 302 protrudes to a greater extent from shield 600.

Needle sheath 700 is disposed at the forward end of system 10, such that needle tip 302 is disposed and sealed within cylindrical body portion 710 of the elastomeric first portion 701 of needle sheath 700. Sleeve portion 736 of second portion 702 of needle sheath 700 is disposed about a forward portion of shield 600, such that the inner surface of sleeve portion 736 engages an outer surface of shield 600. As such, first portion 738 of sleeve portion 736 of needle sheath 700 engages an outer surface of forward portion 610 of shield 600, and second portions 740 of sleeve portion 736 of the needle sheath engages an outer surface of neck portion 608 of the shield. Skin engaging surface 620 of shield 600 is disposed within first circumferential seat 752 and engages rearward facing wall portion 734 of needle sheath 700, and a rearward end of wall portion 736 engages outward facing shoulder 608 of shield 600.

An outer surface of second sleeve portion 746 of needle sheath 700 engages an inner surface of circular bore 622 of shield 600 such that second sleeve portion 746 and tubular sleeve 714 extend into shield 600 and into locking sleeve 500. Specifically, an exterior surface of second sleeve portion 746 of needle sheath 700 is disposed within an interior surface of barrel 502 of the locking sleeve 500. A rearward portion of tubular 714 is disposed within cylindrical seat 142 of needle hub 100, such that an exterior surface of cylindrical cowl 140 engages interior surface 716 of tubular sleeve 714.

As seen clearly in FIGS. 7E and 7F, in the storage operative orientation, tabs 748 of needle sheath 700 are disposed within needle sheath receiving slots 126 on the exterior surface of hub 100, and engage a side surface of inwardly extending guiding teeth 504 of locking sleeve 500, thereby locking inwardly extending guiding teeth 504 in the storage position until removal of the needle sheath and preventing accidental triggering of system 10 during storage and transportation thereof. Locking of the teeth 504 from moving backward, which is required for triggering activation of the system 10, is effected by prevention of rotation of the teeth 504 of locking sleeve 500. Such rotation is required for passing triggering point 112, and is prevented by the presence of tabs 748 in slot 126. Accidental triggering is also prevented by the slot 106 being disposed on hub 100 internally to system 10, and being covered by shield 600, such that a user cannot directly access slot 106 or manipulate the position of guiding teeth 504 along the slot.

Reference is now additionally made to FIG. 8A, which is a model perspective view illustration of system 10, in a ready for use operative orientation, and to FIG. 8B, which is a model perspective view illustration of needle hub 100, needle 300, and locking sleeve 500 of system 10 in the ready-for-use operative orientation.

The ready to use operative orientation illustrated in FIGS. 8A and 8B is identical to the storage operative orientation shown in FIGS. 7A to 7H, with the exception of removal of the needle sheath 700 from the system. As seen in FIG. 7H, in order to transition system 10 from the storage operative orientation shown in FIGS. 7D to 7G, to the ready for use operative orientation shown in FIGS. 8A and 8B, needle sheath 700 is moved in the direction of arrow 800, away from shield 600. As such, in the ready for use operative orientation, tabs 748 are removed from slot 126 and guiding teeth 504 are movable within slot 106, and needle tip 302 is exposed and protrudes slightly out of shield 600.

It will be appreciated that the fact that needle tip 302 protrudes from shield 600 is advantageous as it allows a user to better direct the needle toward the injection site, and when using system 10, to aspirate the syringe through the needle, remove some of the medicament from the syringe, remove air bubbles from the syringe, add medicament to the syringe, or otherwise manipulate the liquid in the syringe by manipulating a plunger of the syringe, without activating the protection mechanism of system 10.

Reference is now made to FIG. 9A, which is a model perspective view illustration of the system 10, in a triggering operative orientation, and to FIG. 9B which is a model perspective view illustration of needle hub 100, needle 300, and locking sleeve 500 of the system 10, in the triggering operative orientation. Reference is additionally made to FIG. 10A, which is a model perspective view illustration of system 10, in a triggering rotation operative orientation, and to FIG. 10B, which is a model perspective view illustration of needle hub 100, needle 300, and locking sleeve 500 of the system 10, in the triggering rotation operative orientation.

In the triggering operative orientation, which occurs when the user begins pressing pushing shield 600 rearwardly in the direction of arrow 802, for example by pressing the shield against the injection site, shield 600 and locking sleeve 500 are guided rearwardly, against the compression force of spring 400. The rearward motion of shield 600 is guided by protrusions 132 of needle hub 100 moving forwardly in hub engaging slots 130, and results in exposure of a greater portion of needle 300.

Due to the rearward motion of locking sleeve 500, guiding teeth 504 of locking sleeve 500 moves along slot 106 of needle hub 100 from forward storage surface 108, along side storage surface 110, thereby rotating slightly against the torsion force applied by spring 400 to triggering point 112, and can now slide along or rotate past triggering surface 114 under the torsion force applied by spring 400 until reaching torque limiting surface 116. Such motion of guiding teeth 504 causes rotation of locking sleeve 500, as seen clearly in FIG. 10B and as indicated by arrow 804.

By sliding along side storage surface 110 of needle hub 100, system 10 reaches safety feature triggering point 112. At this triggering point, the safety feature is irreversibly activated, and once the shield 600 is removed from the injection site the needle 300 will become blocked by the shield, as explained in further detail hereinbelow. On the other hand, if prior to reaching the triggering point 112 the user removes pressure from the shield 600, for example by removing it from the injection site, the system 10 returns to its ready for use operative orientation shown in FIGS. 8A and 8B, due to the release of spring 400 which causes locking sleeve 500 to move forwardly together with shield 600, resulting in guiding teeth 504 of locking sleeve 500 returning to lie against storage surfaces 108 and 110 of slot 106.

It will be appreciated that the exact location of triggering point 112 and of triggering surface 114 of slot 106 determines the extent to which shield 600 may be pressed, and moved rearwardly, prior to activation of the safety feature of system 10. Specifically, when triggering point 112 and triggering surface 114 are located closer to the forward end of needle hub 100, the safety feature is triggered by application of less pressure to shield 600, or the system is more sensitive to pressure, and when triggering point 112 and triggering surface 114 are located closer to the rearward end of needle hub 100, the safety feature is triggered by application of more pressure to shield 600.

Figure 11A:
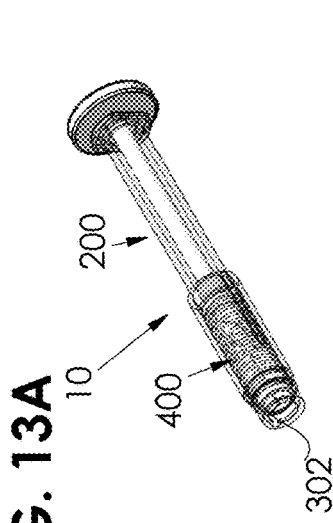
FIG. 11A is a model perspective view illustration of the system of FIG. 1, in an injection operative orientation.
Figure 11B:
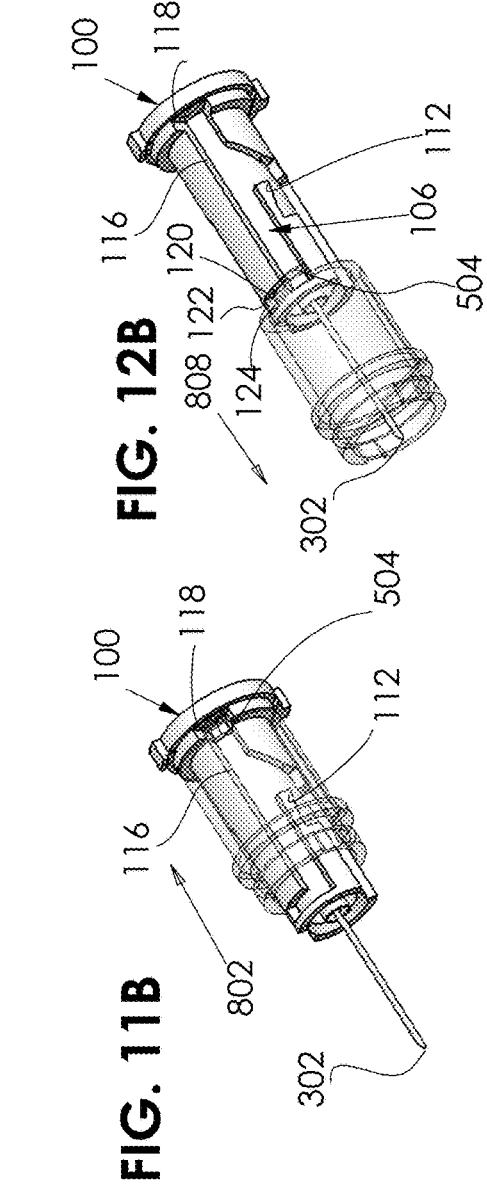
FIG. 11B is a model perspective view illustration of the needle hub, the needle, and the locking sleeve of the system of FIG. 11A, in the injection operative orientation.

Reference is now made to FIG. 11A, which is a model perspective view illustration of system 10, in an injection operative orientation, and to FIG. 11B, which is a model perspective view illustration of needle hub 100, needle 300, and locking sleeve 500 of the system 10, in the injection operative orientation.

In the injection operative orientation, which occurs when the user continues pressing shield 600 against the injection site, typically to the full extent possible, shield 600 and locking sleeve 500 are guided rearwardly, against the compression force of spring 400, in direction 802. The rearward motion of shield 600 is guided by protrusions 132 of needle hub 100 moving rearwardly in within hub engaging slots 630 of shield 600, and results in exposure of a greater portion of needle 300, up to the maximal needle penetration depth.

Due to the rearward motion of locking sleeve 500, guiding teeth 504 of locking sleeve 500 moves rearwardly along torque limiting surface 116 of slot 106 of needle hub 100, away from triggering surface 114 under the torsion force applied by spring 400 to locking sleeve 500. Rearward motion of guiding teeth 504 may continue, as long as additional pressure is applied to shield 600, until spring 400 is fully compressed, until protrusions 132 of needle hub 100 engage a forward end surface of hub-engaging slots 630 of shield 600, or until guiding teeth 504 engage range limiting surface 118 of slot 106 of needle hub 100. When shield 600 is fully depressed surrounding sleeve 500, the needle 300, and particularly needle tip 302, is at its full penetration depth.

Following needle penetration, the user may press a plunger 204 of syringe 200 to inject the fluid contained in syringe 200, as is well known in the art.

It is a particular feature of the present invention that, since shield 600 cannot rotate relative to needle hub 100, but locking sleeve 500 can rotate relative to shield 600, when skin engaging surface 620 of the shield engages a user's skin, and torsion loads of spring 400 are applied to locking sleeve 500, rotation of the locking sleeve does not result in rotation of the shield thus relieving the user from needing to hold the system 10 tightly against the skin to prevent the shield form rotating, and from any discomfort resulting from such rotation. As a result, the loads and forces in system 10 can be greatly reduced.

Figure 12A:
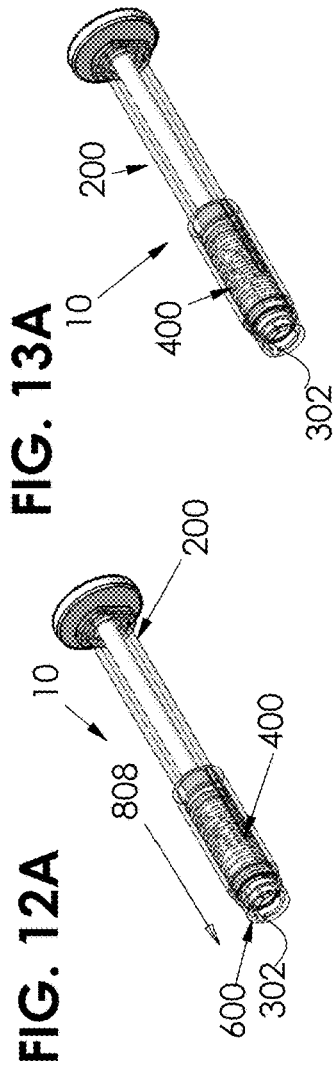
FIG. 12A is a model perspective view illustration of the system of FIG. 1, in a pre-locking operative orientation.
Figure 12B:
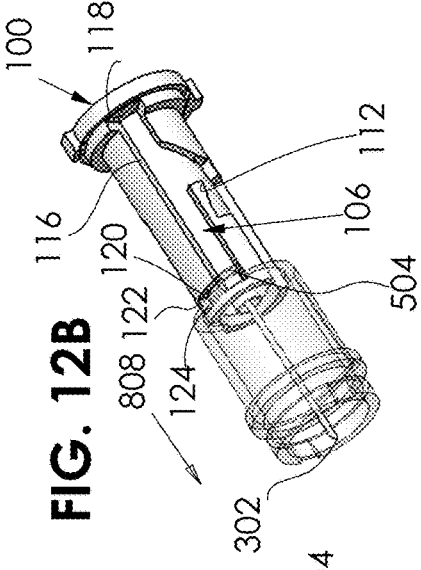
FIG. 12B is a model perspective view illustration of the needle hub, the needle, and the locking sleeve of the system of FIG. 12A, in the pre-locking operative orientation.

Reference is now made to FIG. 12A, which is a model perspective view illustration of system 10, in a pre-locking operative orientation, and to FIG. 12B which is a model perspective view illustration of needle hub 100 needle 300, and locking sleeve 500 of the system 10, in the pre-locking operative orientation.

The pre-locking operative orientation occurs following triggering of the safety feature of system 10, and preferably following injection of any amount of medication from the syringe, whether the full amount or a partial amount thereof (or even no injection at all). Specifically, the pre-locking operative orientation occurs when the user releases the pressure from shield 600, for example by removing system 10 from the injection site, and just before the shield 600 locks around needle 300. As seen clearly in FIG. 12A, following removal of pressure from shield 600, pressure is reduced from spring 400, which decompresses and drives locking sleeve 500 forwardly, together with shield 600, in a direction of arrow 808.

Relative forward motion of shield 600 is guided by relative backward motion of protrusions 132 of needle hub 100 thereof within slots 630 of shield 600. Relative forward motion of locking sleeve 500 results in guiding teeth 504 of locking sleeve 500 moving forwardly along torque limiting surface 116 of slot 106 of needle hub 100 until reaching protection surface 124. When forward facing surfaces 510 of guiding teeth 504 reach the protection surfaces 124, the needle 300, and particularly needle tip 302, is disposed within shield 600.

Figure 13A:
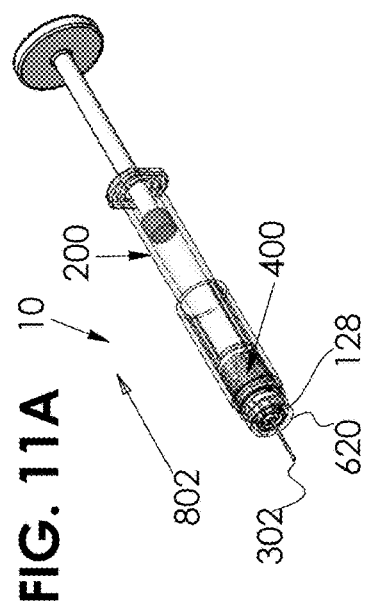
FIG. 13A is a model perspective view illustration of the system of FIG. 1, in locked operative orientation.
Figure 13B:
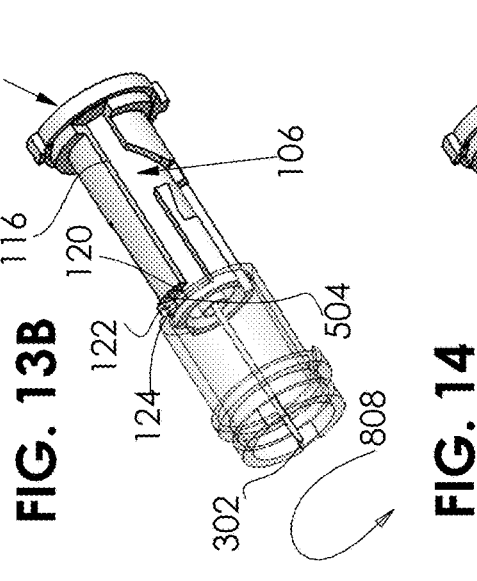
FIG. 13B is a model perspective view illustration of the needle hub, the needle, and the locking sleeve of the system of FIG. 13A, in the locked operative orientation.

Reference is now made to FIG. 13A, which is a model perspective view illustration of system 10, in a locked operative orientation, and to FIG. 13B, which is a model perspective view illustration of needle hub 100, needle 300, and locking sleeve 500 of the system 10, in the locked operative orientation.

The locked operative orientation occurs automatically immediately following the pre-locking operative orientation, without requiring any additional action by the user. As seen, locking sleeve 500 rotates under the torsion force of spring 400 in direction 808, such that guiding teeth 504 of locking sleeve 500 slides along protection surface 124 to end of rotation surface 122 of slot 106. The location of end or rotation surface 122 determines the locking point of system 10.

Figure 14:
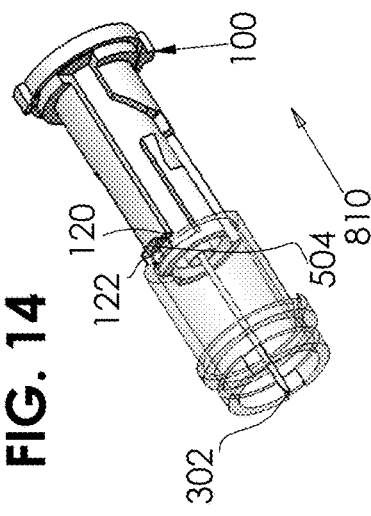
FIG. 14 is a model perspective view illustration of the needle hub, the needle, and the locking sleeve of the system, in needle-protection operative orientation.

Reference is now made to FIG. 14, which is a model perspective view illustration of needle hub 100, needle 300, and locking sleeve 500 of the system 10, in the needle protection operative orientation.

FIG. 14 illustrates the position of needle hub 100 and locking sleeve 500 in a situation in which, following locking of shield 600 over needle 300, a user or any other person intentionally or inadvertently pushes shield 600 in a rearward direction, indicated by arrow 810. For example, the user may hold the system 10 while touching skin-engaging surface 610, and thus may accidentally apply a rearward force to shield 600. Pressure applied by the user moves shield 600 rearwardly in the direction of arrow 810 a little bit, but such movement is limited by guiding teeth 504 of locking sleeve 500 engaging locking surface 120 of slot 106 of needle hub 100. As such, even if the user pushes shield 600 rearwardly after locking of system 10, the needle tip 302 will not be exposed, and there is no risk of needle pricks.

It will be appreciated that the length of locking surface 120 determines the "give", or maneuverability, of the shield 600 when system 10 is in the locked operative orientation, or between the locking operative orientation and the needle protection operative orientation. Specifically, a greater length of locking surface 120 would allow more movement of shield 600 while remaining in the locked operative orientation, whereas a smaller length of locking surface 120 would allow less, or no, movement of shield 600 in the locked operative orientation.

It is a particular feature of the present invention that at all times during use system 10, and in all operative orientation thereof, needle hub 100 including slot 106 and locking sleeve 500 with guiding teeth 504 are disposed within shield 600 and are inaccessible to the user. As such, there is no possibility for the user to manually trigger or manipulate the operation of the system other than by pushing on shield 600 when it is in the ready to use operative orientation, and there if no possibility for the user to re-cock the system following use thereof, without using special or dedicated tools.

FIGS. 15A and 15B are, respectively, a constructed perspective view illustration and a partially exploded view illustration of another system 910 for protection of a needle connected or connectable to a syringe according to an embodiment of the teachings herein, system 910 including system 10 of FIGS. 1 to 14 and a gripper 920.

As seen in FIGS. 15A and 15B, system 910 includes the entirety of system 10, as described hereinabove, as well as the gripper 920. As such, in the following description of system 910, elements of system 10 have the same reference numerals described and shown in FIGS. 1 to 14.

Reference is now made to FIGS. 16A and 16B, which are, respectively, a side view planar illustration and a sectional illustration of a first embodiment of the gripper 920 forming part of system 910 of FIGS. 15A and 15B.

As seen in FIGS. 16A and 16B, the gripper includes a tubular body portion 922, terminating at a forward end thereof in a surface 924, and at a rearward end thereof in finger grips 926. Finger grips 926 are sized and configured such that a user can easily place two fingers, such as the index finger and middle finger, beneath grips 926 in a similar manner to which finger grips of prior art syringes are used.

Adjacent the rearward end thereof, disposed radially between grips 926 and on an inner surface 928 of tubular body 922, are one or more longitudinal slots 930, extending about a quarter of the length of tubular body 922, which are designed to provide a little flexibility to the gripper 920 during mounting thereof on the system 10. Additionally disposed at a rearward facing end of tubular portion 922 is a circumferential radial indentation 932, having an inner diameter greater than the inner diameter of the rest of tubular portion 922.

In use, gripper 920 is disposed about system 10, such that interior surface 928 of gripper body 922 engages an exterior surface of shield 600 and of syringe 200, with grips 926 extending radially outwardly on opposing sides of system 910. Rearward facing flange 206 of syringe 200 is disposed within indentation 932 of gripper 920, and enables snap fit engagement of syringe 200 with gripper 920 while restricting relative axial movement between the syringe 200 and gripper 920. In the storage operative orientation, forward facing surface 924 of gripper 920 reaches approximately the center of the exterior surface of shield 600, such that needle sheath 700 is not enclosed by gripper 920 and is accessible to the user.

Reference is now made to FIG. 17, which is a perspective view illustration of a second embodiment of the gripper 920a forming part of the system 910 of FIGS. 15A and 15B.

As seen in FIG. 17, the gripper 920a may include a barrel 940 having an interior surface 948 and including a slot extending along the entire length of the barrel. Barrel 940 includes a forward portion 942 having a first diameter, and a rearward portion 943 having a second diameter, smaller than the first diameter. It is noted that the diameter of rearward portion 943 may be also identical to, or bigger than, the diameter of forward portion 942. Forward portion 942 terminates in a forward surface 944, and rearward portion 943 terminates in finger grips 946, substantially as described hereinabove with respect to FIGS. 16A and 16B. A bore 952 is formed between finger grips 946, the bore extending all the way through one end of the finger grips.

In use, or preferably during manufacturing at a factory or other manufacturing facility, system 10 is inserted into gripper 920a via the slot in barrel 940, and is disposed within the gripper, such that interior surface 948 of barrel 940 engages an exterior surface of shield 600 and of syringe 200, with grips 946 extending radially outwardly on opposing sides of system 910, and with plunger 204 extending through bore 952 between finger grips 946. Rearward facing flange 206 of syringe 200 is disposed within bore 952 of gripper 920a, thus enabling snap-fit engagement of syringe 200 with gripper 920a while restricting relative axial movement between the syringe 200 and gripper 920a. In the storage operative orientation, forward facing surface 944 of gripper 920a reaches approximately the center of the exterior surface of shield 600, such that needle sheath 700 is not enclosed by gripper 920a and is accessible to the user.

It is noted that the gripper 920 or 920a are each presented herein as a single part, preferably made of a clear plastic, allowing a person a view of the contents of the syringe, the syringe barrel, and various positions of the front end of plunger 204 during the stages of use. Both gripper options 920 and 920a can also be multi-part elements, assembled around the syringe 200, preferably at the manufacturing site. For example, the grips 926 or 946 can be produced from one, preferably opaque, colored material, while the tubular body 922 of gripper 920, or the barrel part 940 of gripper 920a can be produced from a clear, fully transparent, material enabling view of the contents of the syringe, etc. as detailed above.

In system 10 of FIGS. 1 to 14, when transitioning from the storage operative orientation to the ready for use operative orientation by removing needle sheath 700, the user may accidentally push shield 600 in a rearward direction (opposed to the direction of motion of needle sheath 700), and may thereby accidentally trigger needle locking. In system 910, either when using gripper 920 or when using gripper 920a, when the user removes the needle sheath 700, the user holds the gripper, which is fixed relative to the syringe, and which does not influence the location of shield 600, thereby preventing such accidental triggering of the needle sheath in the system 910. This method for prevention of accidental triggering of system 10 by the user enables use of a simpler version of the system 10, in which tabs 748 of needle sheath 700, and/or the tapered shape of surface 110 of needle hub 100 may be eliminated.

Reference is now made to FIGS. 18A to 18D, which are, respectively, a perspective view illustration, two planar view illustrations, and a sectional illustration of a unified syringe and needle hub 20 usable in a system similar to system 10 of FIGS. 1 to 14.

As seen in FIGS. 18A to 18D, the unified syringe and needle hub 20 includes a needle hub portion 101, similar to needle hub 100 described hereinabove and including a slot 106 having multiple surfaces as described herein, and a rearward syringe portion 201 including a hollow syringe as described herein. The unified syringe and needle hub 20 is formed of a single piece of material, which may, for example, be injection molded. A hollow of syringe portion 201 extends into hollow 138 of needle hub portion 101, such that needle 300 seated in needle hub portion 101, is in fluid communication with the hollow of syringe 201. The unified syringe and needle hub 20 may replace syringe 200 and needle hub 100 in system 10, with all other components, and all functionality of the system, remaining as described hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A needle protection system, adapted to protect a tip of a hypodermic needle connected or connectable to a syringe, the system comprising:
   a shield adapted, in a protected operative orientation of said needle protection system, to shield the tip of the hypodermic needle;
   a needle hub engaged to the hypodermic needle and having an exterior surface including at least one slot, said slot including at least three surfaces corresponding to three operative orientations of said needle protection system, said needle hub being connected to said shield such that said shield can move axially, but cannot rotate, relative to said needle hub; wherein said three operative orientations include a storage operative orientation, an injection operative orientation, and a needle protection operative orientation;
   a locking sleeve functionally associated with said shield, such that said locking sleeve can rotate, but cannot move axially, relative to said shield, said locking sleeve including at least one guiding tooth disposed within said at least one slot of said needle hub and movable relative thereto, between said surfaces, so as to transition said shield between said three operative orientations of said needle protection system;
   at least one biasing element, adapted for axial biasing of said shield; and
   a needle sheath, adapted to be disposed about an end of said shield;
   wherein said needle sheath includes at least one tab, said at least one tab adapted, in said storage operative orientation, to be disposed within said slot and prevent said at least one guiding tooth from moving between said surfaces.

2. The needle protection system of claim 1, wherein said shield surrounds said needle hub and said locking sleeve, such that in all said three operative orientations said at least one slot of said needle hub is covered at least by a portion of said shield.

3. The needle protection system of claim 1, wherein said shield surrounds said needle hub and said locking sleeve, such that in all said three operative orientations said at least one slot of said needle hub is covered at least by a portion of said shield.

4. The needle protection system of claim 1, further comprising the syringe in fluid communication with the needle, said syringe being fixedly connected to said needle hub.

5. The needle protection system of claim 1, wherein said biasing element is disposed between said needle hub and said locking sleeve, and is adapted to apply forces to said locking sleeve.

6. The needle protection system of claim 1, wherein said biasing element includes a torsion force adapted for relative rotation between said locking sleeve and said needle hub, and wherein said locking sleeve rotates, thereby provide said relative rotation.

7. The needle protection system of claim 1, wherein, in said storage operative orientation, a tip of the hypodermic needle protrudes from said shield, in said injection operative orientation the hypodermic needle protrudes from said shield to a greater extent than in said storage position, and in said needle protection operative orientation the tip of the hypodermic needle is disposed within said shield and is locked therein.

8. The needle protection system of claim 1, wherein said at least three surfaces include:
at least one storage surface corresponding to said storage operative orientation;
a end-of-press surface corresponding to said injection operative orientation; and
a locking surface corresponding to said needle protection operative orientation,
wherein said storage surface, said end-of-press surface, and said locking surface are at different positions along a longitudinal axis of said needle hub.

9. The needle protection system of claim 1, wherein transition of said system from said storage operative orientation to said injection operative orientation is achieved by application of pressure to said biasing element, and wherein transition of said system from said injection operative orientation to said needle protection operative orientation is achieved by removal of pressure from said biasing element, and wherein said application of pressure to said biasing element comprises application of pressure to said shield, and removal of pressure from said biasing element comprises removal of pressure from said shield.

10. The needle protection system of claim 9, wherein said slot includes a triggering point, and wherein said transition of said system from said storage operative orientation to said injection operative orientation and to said needle protection operative orientation occurs only if said pressure applied to said biasing element is sufficient for pushing said guiding tooth past said triggering point.

11. The needle protection system of claim 10, wherein if said pressure applied to said biasing element is released prior to said guiding tooth passing said triggering point, said needle protection system returns to said storage operative orientation.

12. The needle protection system of claim 10, wherein:
said slot includes a one-way triggering passage terminating in said triggering point;
said one-way triggering passage allows passage of said guiding tooth from said storage surface toward said triggering point; and
once said guiding tooth has passed said triggering point, rotation of said guiding tooth relative to said slot blocks passage of said guiding tooth back toward said storage surface.

13. The needle protection system of claim 9, wherein:
said slot includes a one-way locking passage terminating in said locking surface;
said one-way locking passage allows passage of said guiding tooth from said end-of-press surface toward said locking surface; and
once said guiding tooth has passed a locking point, said one-way locking passage blocks passage of said guiding tooth therein toward said end-of-press surface.

14. The needle protection system of claim 1, wherein said needle sheath includes at least one elastomeric portion such that, in said storage operative orientation, a tip of the hypodermic needle extending out of said shield is disposed and sealed within said elastomeric portion.

15. The needle protection system of claim 1, further comprising a gripping element disposed about at least part of said shield and adapted for user gripping thereof during operation of said needle protection system, said gripping element being axially fixed relative to said syringe, and said shield being axially movable relative to said gripping element.

* * * * *